United States Patent [19]

Hoey

[11] 4,069,366
[45] * Jan. 17, 1978

[54] PERMEABLE POLYMERIC LINER ON ABSORBENT PADS

[75] Inventor: Charles E. Hoey, Marlton, N.J.

[73] Assignee: Rohm and Haas Company, Philadelphia, Pa.

[*] Notice: The portion of the term of this patent subsequent to Aug. 26, 1992, has been disclaimed.

[21] Appl. No.: 726,716

[22] Filed: Sept. 24, 1976

Related U.S. Application Data

[60] Division of Ser. No. 562,271, March 26, 1975, which is a division of Ser. No. 394,601, Sept. 5, 1973, Pat. No. 3,901,240, which is a continuation-in-part of Ser. No. 354,062, April 24, 1973, Pat. No. 3,887,408.

[51] Int. Cl.$^2$ ............................................. B32B 3/26
[52] U.S. Cl. .................................... 428/310; 428/213; 428/314; 428/315; 428/332; 428/339; 428/913
[58] Field of Search ............... 428/310, 311, 314, 315, 428/913, 332, 339

[56] References Cited

U.S. PATENT DOCUMENTS 3,901,240  8/1975  Hoey ................................... 428/247

Primary Examiner—William J. Van Balen

[57] ABSTRACT

A flexible, absorbent pad having a laminate structure comprising a top layer of a crushed foam of an addition polymer derived from an aqueous polymer latex, an underlying layer of liquid-absorbent material, and a bottom layer of a moisture-impervious film or a gauze. The addition polymer has a soft monomer component containing butadiene, ethylene/vinyl acetate, ethylene/vinyl chloride, propylene/vinyl acetate or propylene/vinyl chloride.

7 Claims, 4 Drawing Figures

← CRUSHED FOAM
← ABSORBENT LAYER
← GAUZE

PERMEABLE POLYMERIC LINER ON ABSORBENT PADS

This is division, of application Ser. No. 562,271 filed Mar. 26, 1975. The latter application is a division of application Ser. No. 394,601, filed Sep. 5, 1973, now U.S. Pat. No. 3,901,240. The patent issued on a continuation-in-part application of application Ser. No. 354,062, filed Apr. 24, 1973, now U.S. Pat. No. 3,887,408.

This invention relates to an absorbent article having a top layer of a crushed polymer latex foam bonded to either a non-woven which is bonded to an absorbent layer or bonded directly to the absorbent layer, and which in turn is bonded to either a flexible, liquid impermeable bottom layer such as polyethylene or to a woven or non-woven gauze. The laminate of the foam and the non-woven layer or absorbent layer is self-bonded; i.e., no extraneous adhesive is needed. The liquid impermeable bottom layer such as polyethylene or the gauze bottom layer may be wider than the absorbent material but is generally of a width such that the absorbent layer and foam self-bond.

In the past, similar laminates have been made with a permeable top layer such as adhesively bonded fibers, and even a fully expanded foam such as polyurethane foam. However, the foam is either of such light weight or low density that a fabric-like hand could not be obtained. Alternatively, if a dense foam is applied by controlling the amount of foaming agent or the extent of expansion, the product is relatively rubbery and non-fabric-like or stiff and inflexible and does not have the hand of a soft fabric, or the desired porosity.

Examples of such prior art of polyurethane foams are shown in U.S. Pat. Nos. 3,431,911; 3,461,872; 3,463,745; 3,512,530, and 3,563,243. It should be noted in those patents that illustrate the foams that the open cells defined by the ribs or struts are essentially symmetrical and three-dimensional. Thus, when the foam is stretched, for example, when an attempt is made to flush the absorbent lining covered with a fully expanded open-celled foam layer, the foam layer is susceptible to extensive elongation before reaching the limits of its tear strength. Such polyurethane foams tend to ball up or form ropes and clog the plumbing.

The present invention, by using foams with mainly two dimensional flat open cells, permits tearing of the crushed foam under moderate elongation, but provides good integrity at the low elongations (<50 percent) encountered in normal use.

In general, the invention relates to a flexible absorbent pad comprising a top layer of polymer foam material which is permeable to liquids, an underlying layer of liquid absorbent material and a bottom film of flexible, moisture impervious material, the improvement in which said polymeric foam material is crushed foam of an addition polymer derived from an aqueous polymer latex, the thickness of the crushed layer being from about 1 mil to about 10 mils preferably the horizontal face of the dry, crushed foam has a pore size which is less than about 10 mils with approximately 100,000 to 1,000,000 pores per square inch and in which the laminate has good wet strength and dry strength at a low elongation but which when held by the film, placed in a body of water and pulled, the crushed foam splits and tears and the absorbent material breaks up thus providing a flushable product.

The addition polymer employed is preferably a crosslinked thermoset foam and the absorbent material is fibrous, which permits intimate intertwining of the fiber and the foam at their juncture but with a substantial thickness of the absorbent material free of foam and with a substantial thickness of the foam free of fiber.

This invention also comprises having a non-woven layer between the crushed foam layer and absorbent layer. This type of pad is more comfortable than one in which the non-woven comes in direct contact with the skin.

Also, the invention comprises having the moisture impervious layer replaced with a gauze. This type of pad would be employed when it is desirable to allow air to circulate through the pad, such as in a wound dressing.

Figure 1:
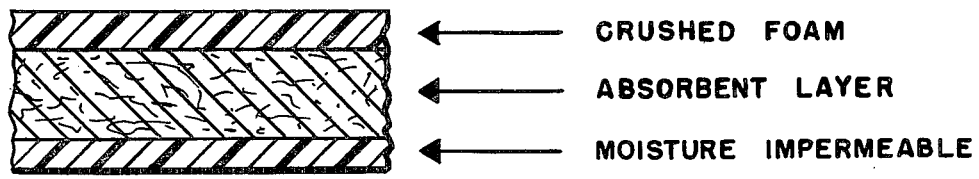
FIG. 1 illustrates the basic absorbent pad having a crushed foam upper layer which is bonded to a moisture impermeable layer thereby encapsulating an absorbent layer.
Figure 2:
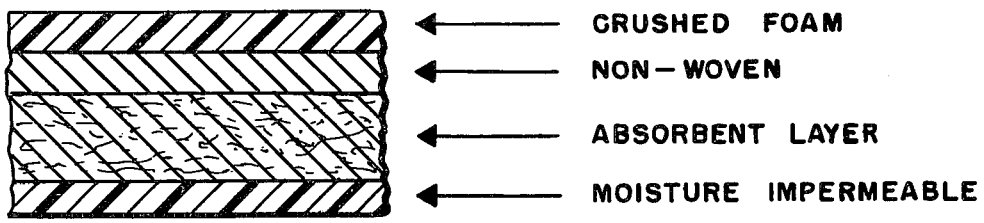
FIG. 2 illustrates a pad in which a non-woven layer is coated with a crushed foam which layers are bonded to a moisture impermeable layer thereby encapsulating an absorbent layer.
Figure 3:
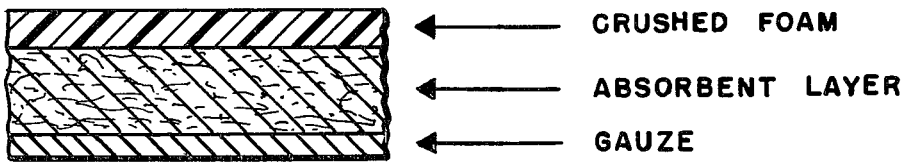
FIGS. 3 and 4 illustrate the pads of FIGS. 1 and 2, respectively, having a woven or non-woven gauze in place of a moisture impermeable layer.
Figure 4:
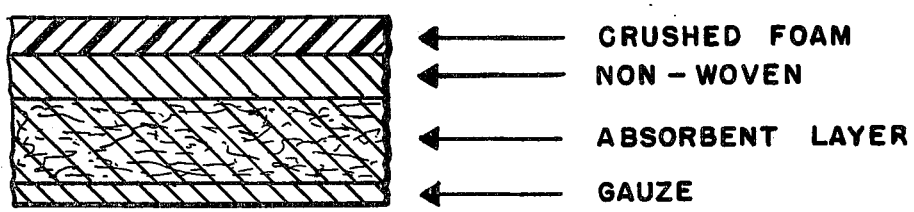

The term "non-woven" as employed herein means those fabrics produced from staple fibers or continuous filaments without the use of conventional weaving or knitting operations. For a further description of the type of non-woven which may be employed, reference is made to U.S. Pat. Nos. 2,931,749; 2,982,682; 3,074,834; 3,101,292 and 3,521,638. These references insofar as they define the term "non-wovens" are herein incorporated by reference.

In a specific preferred embodiment, a crosslinkable or thermosettable acrylic latex foam is deposited onto release paper coated with a silicone release coating, and the foam is dried without thermosetting. The latex is foamed, preferably mechanically by using air and employing a foam stabilizer. The foam is applied to the release surface and dried without causing crosslinking. The foamed layer and the absorbent material are then juxtaposed, the foam is crushed by pressure, with or without embossing a design in the laminate, and then heated to a temperature sufficiently high to crosslink and thermoset the polymers.

The absorbent medium may be bonded to the waterproof film but is preferably incapsulated between the waterproof film and the crushed foam layer or the non-woven containing a crushed foam surface. When a flushable composite is dipped in water, the crushed foam surface or crushed foam top-coated non-woven and the absorbent medium pull away from the film generally leaving a small residue of adhesive on the water-impervious film at the glue line.

In another specific preferred embodiment when crushed foam is to be used as an aesthetically appealing surface over a conventionally bonded non-woven, the wet foam can be cast on a release medium as previously described and subsequently adhered to the non-woven by laminating and simultaneously crushing the foam against the non-woven as described in the case of combining the crushed foam to an absorbent wadding. Alternately, the wet foam can be cast directly onto the non-woven so that the foamed non-woven can then be passed through nip rollers to crush the foam. As opposed to non-wovens which generally contain between 25 to 40% resin solids and 75–60% fiber in order to provide sufficient strength, the lamination of a crushable foam to a non-woven permits the use of reduced amounts of resin applied to the non-woven via saturation, print bonding or beater deposition. The crushed foam treated non-woven can be cured after the composite has been made to achieve more complete crosslinking of the foam.

This procedure affords an improved flexible absorbent pad which comprises a top layer of a non-woven over a liquid absorbent material and a bottom film of flexible moisture impervious material wherein the improvement comprises having a crushed foam layer having a thickness of from 1–10 mils of an addition polymer derived from an aqueous polymeric latex on the top of the non-woven layer. This is a preferred absorbent pad because it provides a soft, dry velvet-like texture to the surface of the non-woven which is much more comfortable when used in contact with the skin. When it is desired to use the crushed foam coated material as a wound dressing the outer layer of the moisture impervious film is replaced with a woven or non-woven gauze.

The foam initially has a wet foam density of from about 0.05 to 0.5 grams per cubic centimeter and is applied in a thickness of from about 4 to about 45 mils, and preferably at a thickness of no more than 30 mils. The density, of course, will vary with the presence or absence of pigments and fillers and their identity. The foam is then dried without causing thermosetting, crosslinking or vulcanization to a sensibly dry condition, for example, to an air-dry or sensibly dry state, for example, by heating at a temperature below that which causes thermosetting, crosslinking, or vulcanization. For example, by drying for a period of time of from 1 to 10 minutes at an oven temperature in the range of from about 200° to 350° F., followed by placing the absorbent material and the surface of the foam together and then crushing the foam to a thickness of from 5 percent to 35 percent of its original dry thickness to afford a foam with a density of from about 0.2 to about 3 g./cc., followed by curing of the crushed foam. In general, the thickness of the dried foam prior to crushing may be less than that of the wet foam, due to shrinkage. This shrinkage may be up to 30 percent of the thickness of the wet foam. Suitable moisture contents range from 5 percent to 20 percent in order to qualify as air dry or sensibly dry materials. The criteria as to moisture content is that the foam must be stable enough to be self-bonded to the absorbent material. In some cases crosslinking may be accomplished by catalysis rather than primarily by the application of heat. Of course, the foam may be crushed before it is self-bonded to the absorbent material, but in this case a crushing roll having a release coating such as a silicone or Teflon is desirable. Normally no adhesive is needed between the foam and the absorbent layer, since preferably a thermosettable foam is used, and the final curing of the foam causes a firm bond between the layers.

The crushed foam composite is designed so that it disintegrates upon flushing in a sewage system when used as an absorbent diaper or as a sanitary napkin. Crushed foam composites can also be used for wound dressing which do not adhere to human tissue because of the complete lack of fiber on the exposed surface and porosity allowing wound exudate to penetrate the foam into the adsorbent medium. The cohesive strength of the crushed foam lining is low so that any of the lining which becomes permanently entrained during scab formation of a wound will separate away from the remainder of the composite without damaging the wound. In addition, to enhance the comfort of non-woven linings, crushed foam can be used as a topcoat on the non-woven where it is self-adhering as previously described. The crushed foam imparts a velvet-like texture to the surface of the non-woven and prevents fibers from coming in contact with the user. In addition, the crushed foam enhances the surface dryness of the composite. The crushed foam surface can also serve as part of the binding system for the non-woven permitting reduced usage of conventional binders normally applied by saturation, printing or beater deposition. Beneficial additives can be incorporated into the foaming mix before casting, such as germicidal additives, deodorants, reodorants, fillers to enhance comfort such as talc or fire resistance such as aluminum hydrate and dissipate static electricity for use in operating rooms.

Of course, a thermoplastic foam may be used. Crushed foam is essential, since if the initial foam is formed to the final density by control of the amount of foaming agent or by means such as using a chemical blowing agent and restraining the expansion in order to get the final density, the walls or struts connecting the air spaces are relatively thick. A crushed foam, on the other hand, initially having expanded to a number of times its final thickness, has thin connective walls or struts. The result is that the crushed foam is much more flexible and fabric-like than a foam initially expanded to the density noted above. These foams are inherently opaque. The opacity can be compared with the opacity of whipped egg whites; the liquid egg white is substantially transparent and the gas cells incorporated therein confer opacity of whipped egg whites.

When pigmented compositions are contemplated, examples of the pigments that may be employed include clays, especially of the kaolin type, calcium carbonate, blanc fixe, talc, titanium dioxide, colored lakes and toners, ochre, carbon black, graphite, aluminum powder or flakes, chrome yellow, molybdate orange, toluidine red, copper phthalocyanines, such as the "Monastral" blue and green lakes. If dyed compositions are used, examples of dyes for acrylic film and foam include basic and dispersed dyes. Other composites could be made dyeable, if not inherently so, through the use of additives such as methyl cellulose, polyvinyl pyrollidone, hydroxyl ethyl cellulose, and the like. Other dyes which could be used include acid dyes, vat dyes, direct dyes, and fiber reactive dyes.

An important advantage in utilizing a dried but uncured foam of a crosslinkable polymer and an absorbent layer such as opened cellulose is that the two elements can be passed through the nip of a pair of rollers, the distance between which is small enough to "marry" the two but insufficient to crush the dried foam, all without using an adhesive to bond the foam. Of course, bonding of the dry foam and the absorbent material can be done at a pressure sufficient to crush the foam with or without embossing the same. Even after crushing, the foam has sufficient resilience to be embossed with a patterned roller. If desired, the embossing roller may be heated to the curing temperature of the foam.

For a description of suitable conventional foaming procedures and foam stabilizers and foaming agents, reference is made to Mage, E. W., "Latex Foam Rubber," John Wiley and Sons, New York (1962) and Rogers, T. H , "Plastic Foams", Paper, Reg. Tech. Conf., Palisades Sect., Soc. Plastics Engrs., New York, November, 1964. Most common are the alkali metal, ammonia, and amine soaps of saturated or unsaturated acids having, for example, from about 12 to about 22 carbon atoms. Examples of suitable soaps include tallow soaps and coconut oil soaps, preferably the volatile amine or ammonia soaps, so that the volatile portion is vaporized from the foam. Other useful foaming-foam-stabilizing agents include lauryl sulfate-lauryl alcohol, lauryl sulfate-lauric acid, sodium lauryl sulfate, and other commonly used foamed stabilizers or foaming agents.

The latex, when formulated with the foam stabilizer and optionally, suitable pigments, is readily convertible into the foamed state. The polymer composition is such that excessive thickening of the formulation is not encountered under the acid or alkaline conditions employed to assure the most efficient operation of the foam stabilizing agent. In addition the copolymer is such that the crushed foam retains its softness and its flexibility at low temperatures at least to a temperature as low as 10° F., and after curing is non-tacky.

Important properties of the copolymer are its toughness and flexibility and the minimum film-forming temperature (MFT) of the formulated coating composition, both dependent in large part upon the influence of its monomer composition. The glass transition temperature (Tg) of the copolymer depends upon the selection of monomers and proportions thereof because of their influence on the Tg. "Tg" is a conventional criterion of polymer hardness and is described by Flory, "Principles of Polymer Chemistry," pp. 56 and 57, (1953), Cornell University Press. While actual measurement of the Tg of copolymers may be made, it may be calculated as described by Fox, Bull. Am. Physics Soc. 1, p. 123 (1956). Examples of the Tg of high molecular weight homopolymers and the inherent Tg thereof which permits such calculations are as follows:

| Homopolymer of | Tg |
|---|---|
| n-octyl acrylate | −80° C. |
| n-decyl methacrylate | −60° C. |
| 2-ethylhexyl acrylate | −70° C. |
| octyl methacrylate | −20° C. |
| methyl acrylate | −9° C. |
| n-tetradecyl acrylate | 20° C. |
| methyl methacrylate | 105° C. |
| acrylic acid | 106° C. |

These or other monomers are blended to give the desired Tg of the copolymer. As is known, for a given number of carbon atoms in the alcohol moiety, the extent and type of branching markedly influences the Tg, the straight chain products giving the lower Tg.

One of the monomers utilized to prepare the waterinsoluble addition copolymer is a flexibilizing or "soft" monomer which may be represented by the following formula:

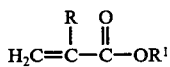
(I)

wherein R is H or alkyl having 1 to 4 carbon atoms and $R^1$ is the straight chain or branched chain radical of a primary or secondary alkanol, alkoxyalkanol or alkylthiaalkanol, the alkanol having from 2 to about 14 carbon atoms, the chain length depending upon the identity of R, examples being ethyl, methylpropyl, n-butyl, 2-ethylhexyl, heptyl, hexyl, octyl, propyl, 2-methylbutyl, 1-methylbutyl, butoxybutyl, 2-methylpentyl, methoxymethyl, ethoxyethyl, cyclohexyl, n-hexyl, isobutyl, ethylthiaethyl, methylthiaethyl, ethylthiapropyl, n-cotyl, 6-methylnonyl, decyl, dodecyl, and the like. When R is alkyl and $R^1$ is alkyl, $R^1$ should have from about 6 to about 14 carbon atoms and when R is H and $R^1$ is alkyl, $R^1$ should have from 2 to about 12 carbon atoms, in order to qualify as a soft monomer. Also, butadiene may be employed. In addition, copolymers such as those prepared from ethylene or propylene and vinyl acetate or vinyl chloride may be employed.

In addition to the flexibilizing monomer, the other essential monomers are the "toughening" or "hard" monomers, discussed in greater detail below and including, for example, monovinyl aromatic monomers, certain acrylic acid and/or methacrylic acid esters, vinyl halides, vinyl nitriles, and, if used, the monomers having hydroxyl, carboxyl, amino, amido epoxy, or other functionality described below. The hardness or softness of the acid and other functional monomers is not critical because of the small amounts used. Styrene and vinyltoluene are examples of the monovinyl aromatics.

The unsaturated carboxylic acid, the preferred functional monomer, may be a simple monocarboxylic acid, or may be a half ester or half amide of an $\alpha,\beta$-unsaturated dicarboxylic acid, and salts thereof with a volatile base such as ammonia, or with a volatile water-soluble amine such as dimethylamine, triethylamine, triethanolamine, morpholine, N-methyl morpholine, picoline, and the like. Examples of copolymerizable ethylenically unsaturated monocarboxylic or polycarboxylic acids are sorbic, cinnamic, vinyl furoic, $\alpha$-chlorosorbic, p-vinylbenzoic, acrylic, methacrylic, maleic, fumaric, aconitic, atropic, crotonic, and itaconic acid, or mixtures thereof, with itaconic acid and the $\alpha,\beta$-unsaturated monocarboxylic acids, particularly methacrylic acid and acrylic acid, being preferred. Other copolymerizable acid monomers include the alkyl half esters or partial esters of unsaturated polycarboxylic acids such as of itaconic acid, maleic acid, and fumaric acid, or the partial amides thereof. Preferred half esters are the lower alkyl ($C_1$ to $C_6$) esters such as methyl acid itaconate, butyl acid itaconate, methyl acid fumarate, butyl acid fumarate, methyl acid maleate, and butyl acid maleate. Such partial esters and partial amides are considered to be "$\alpha,\beta$-unsaturated monocarboxylic acids," and the term as used herein includes such esters and amides.

In addition to or in place of the acids, amides such as acrylamide and methacrylamide, 2-sulfoethyl methacrylate, the materials disclosed in U.S. Pat. Nos. 3,446,777 to W. D. Emmons, 3,150,118 to D. H. Clemens, and 3,266,930 to W. D. Emmons and E. Hankins Owens, and various other functional, polar, or monomers having groups which remain reactive after the polymer is formed, for example, falling within the definitions of Formulas II, III, IV, V, and VI, are also useful, as follows:

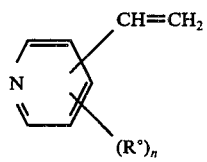 (II)

wherein R° is selected from the group consisting of H and alkyl groups having 1 to 4 carbon atoms, and n is an integer having a value of 1 to 4, $$CH_2=C(R)AYNR^1R^2 \qquad (III)$$

wherein R is selected from the group consisting of H and $CH_3$,

A is selected from the group consisting of O, S,

Y is an alkylene group having 2 to 4 carbon atoms, $R^1$ is selected from the group consisting of H and an alkyl group having 1 to 4 carbon atoms, and $R^2$ is selected from the group consisting of H and an alkyl group having 1 to 4 carbon atoms,

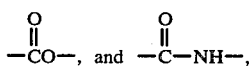 (IV)

wherein R is the same as above, and

Z is an alkylene group having 2 to 3 carbon atoms.

Examples of compounds of Formula II include: 2-vinylpyridine; 4-vinylpyridine; 2-methyl-5-vinylpyridine; 5-methyl-2-vinylpyridine; 4-methyl-2-vinylpyridine; 2-ethyl-5-vinylpyridine; 2,3,4-trimethyl-5-vinylpyridine; 3,4,5,6-tetramethyl-2-vinylpyridine; 3-ethyl-5-vinylpyridine; 2,6-diethyl-4-vinylpyridine.

Examples of compounds of Formula III include: dimethylaminoethyl acrylate and methacrylate; diethylaminoethyl acrylate and methacrylate; dimethylaminopropyl acrylate. and methacrylate; diethylaminopropyl acrylate and methacrylate; dipropylaminoethyl acrylate and methacryalte; di-n-butylaminoethyl acrylate and methacrylate; di-sec-butylaminoethyl acrylate and methacrylate; di-t-butylaminoethyl acrylate and methacrylate; dimethylaminoethyl vinyl ether and sulfide; diethylaminoethyl vinyl ether and sulfide; aminoethyl vinyl ether and sulfide; monomethylaminoethyl vinyl ether and sulfide; N,N-dimethylaminoethyl acrylamide and methacrylamid; N,N-diethylaminoethyl acrylamide and methacrylamide.

Examples of compounds of Formula IV include:
N-[β-(α-methacryloxyaacetamido)ethyl]-N,N'-ethyleneurea;
N-[β-(α-acryloxyacetamido)ethyl]-N,N'-ethyleneurea
N-[β-(α-acryloxyacetamido)ethyl]-N,N'-trimethyleneurea;
N-[-β-(α-methacryloxyacetamido)ethyl]-N,N'-trimethyleneurea.

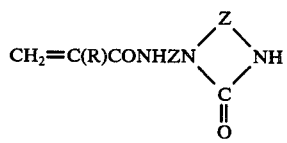 (V)

wherein R and Z are as defined above, of which an example is N-[β-(methacrylamido)ethyl]-N,N'-ethyleneurea.

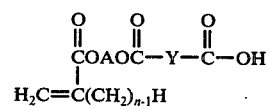 (VI)

wherein

A is an alkylene group having 2 to 10 carbon atoms, preferably 2 to 3 carbon atoms, of which at least 2 extend in a chain between the adjoining oxygen atoms, Y is selected from the group consisting of $$-CH_2-CH_2-, \quad -CH=CH-$$

and ortho-phenylene, and n is an integer having a value of 1 to 2.

Examples of compounds of Formula VI include methacryloxyisopropyl acid maleate, methacryloxyethyl acid phthalate, methacryloxypropyl acid succinate, methacryloxydecyl acid succinate, and metharyloxyoctyl and phthalate.

While the preferred polymers are thermoplastic, crosslinkable or thermosetting polymers, those subject to latent crosslinking are also useful.

There are essentially two types of latent crosslinking which can be used. These are (1) crosslinking subsequent to polymerization by including monomers in the polymer recipe which have functional groups capable of crosslinking by various mechanic including self-crosslinking, or mutual crosslinking by different functional groups, both in the polymer chains, and (2) latent crosslinking by means of an external separately added chemical compound. Combinations can be used.

Where addition polymers are involved, monomers which are suitable for latent crosslinking include certain acrylics having crosslinkable functionality exemplified below.

Examples of the crosslinking reactions which are possible using heat, aging, and/or catalysis are:

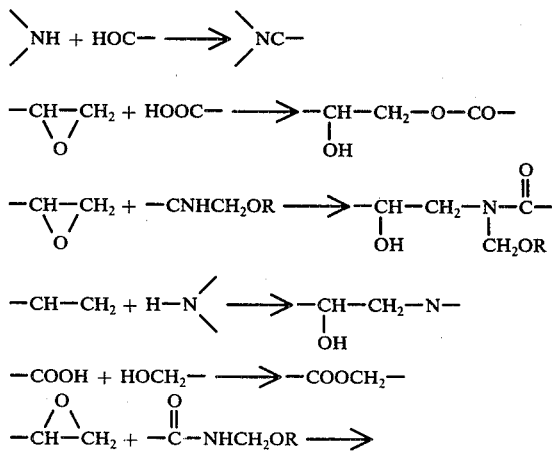

-continued

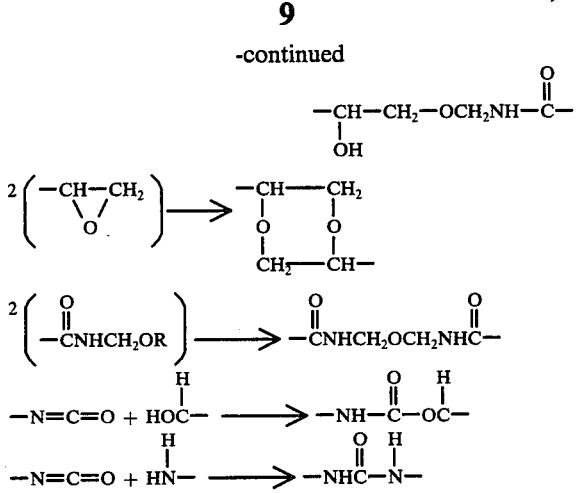

In the above, R is H or CH₃. Addition polymerizable unsaturated monomers containing such groups are well known in the art, examples being isocyanates such as isocyanatoethyl methacrylate, epoxy compounds such as glycidyl methacrylate, aminoalkyl compounds such as methylaminoethyl methacrylate, and t-butylaminoethyl methacrylate, amides such as methacrylamide, guanamines such as 4-pentenoguanamine, hydroxyalkyl esters such as hydroxypropyl methacrylate and hydroxyethyl methacrylate, nitriles such as methacrylonitrile, N-alkoxyalkyl amides such as methoxymethyl methacrylamide, hydroxylalkyl amides such as N-methylol methacrylamide, the analogs of the above methacrylic acid derivatives with other unsaturated acids such as acrylic acid and itaconic acid, such acids themselves, dicarboxylic acids such as maleic acid and half esters and half amides thereof, vinyl ethers of glycols such as ethylene glycol, and so forth.

The crosslinkable addition polymerizable unsaturated monomers have reactive polar groups selected from these including

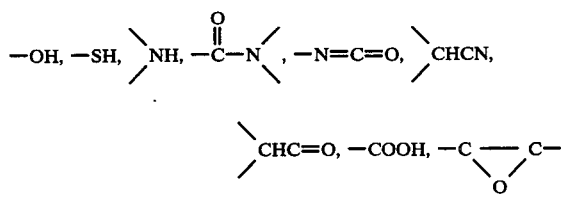

Such groups may be included as are mutually or self-crosslinkable, or separate crosslinking compounds such as a triazine-formaldehyde resin may be added.

Of course, water sensitive materials such as isocyanates should not be used in aqueous systems unless they are blocked by groups such as phenol groups which protect the isocyante groups until subsequent heating or the use of other reaction mechanisms such as the use of calcium, zinc, or tin compound catalyst conventional in the art.

The separate added crosslinker, when used, is useful with or without the use of mutual crosslinking groups and self-crosslinking groups. Among the external crosslinking methods or compounds is the use of organic peroxides such as benzoyl peroxide; the use of epoxy resins such as that obtained from bis-phenol A and epichlorohydrin; esterification, by means of dicarboxylic acids reacting with hydroxyl groups in the polymers, or by reacting diols or polyols such as neopentyl glycol, trimethylol propane, trimethylol ethane, or ethylene glycol with carboxyl groups in the polymer; use of aminoplasts such as melamine formaldehyde, urea formaldehyde, or butylated melamine formaldehyde; diamines and polyamines such as hexamethylene diamine, ethylene diamine, and the Versamids; polyisocyanates such as toluylene diisocyanate; compounds with mixed functionality such as ethanolamine, and other well-known external crosslinkers.

Other ethylenically unsaturated copolymerizable monomers present are the "hard" or toughening monomers. These may be represented by the formula:

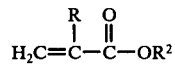

wherein R is as above. R² is preferably alkyl and is methyl or alkyl having from about 13 to about 20 carbon atoms when R is H, and is alkyl of from 1 to about 5 carbon atoms or alkyl of from about 15 to about20 carbon atoms when R is methyl. It can be seen from above that for alkyl acrylates and alkyl methacrylates the Tg at first decreases with an increased chain length of the alkyl group and then the Tg again increases; i.e., both hard and soft monomers are known to occur in each group of esters. Examples of these hard monomers and other hard monomers include: methyl acrylate, vinyl acetate, tetradecyl acrylate, pentadecyl acrylate, methyl methacrylate, ethyl methacrylate, t-butyl acrylate, styrene vinyltoluene, butyl methacrylate, and pentadecyl methacrylate.

The coating compositions are useful as clear coatings or they may be pigmented with a variety of pigments as set forth hereinafter.

Minimal amounts of the functional monomers discussed heretofore having hydroxyl, carboxyl, amino, amido, or epoxy groups and the like, when used, are beneficial in promoting adhesion and in some cases providing thermosettability. The maximum proportion of such monomers based on total monomers is 10 percent, preferably a maximum of about 5 percent. Excessive amounts of some of these monomers contribute to hydrophilicity of the polymer; if the polymer is excessively hydrophobic or hydrophilic, coatings thereform may be undesirable properties.

If it is desired to increase the viscosity of these lactices, they may be readily thickened with various thickeners such as the water-soluble gums. Thus, the ammonium or lower amine salts of polycarboxylic acids are suitable, and typical examples are ammonium polyacryate, ammonium polymethacryalte, the salts of polyacrylalic and polymethacrylic acids with mono-, di-, and trimethylamine, the salts of polyacrylic and polymethacryalic acids with mono-c di-c and triethylamine, etc.

The preferred emulsion copolymers for the foam have a molecular weight of between about 70,000 and 2,000,000, and preferably between about 250,000 and 1,000,000 and are made by the emulsion copolymerization of the several monomers in the proper proportions. Conventional emulsion polymerization techniques are described in U.S. Pat. Nos. 2,754,280 and 2,795,564. Thus, the monomers may be emulsified with an anionic, a cationic, or a nonionic dispersing agent, about 0.05 percent to 10 percent thereof ordinarily being used on the weight of the total monomers. The acid monomer and many of the other functional or polar monomers may be soluble in water so that the dispersing agent serves to emulsify the other monomer or monomers. A polymerization initiator of the free-radical type, such as ammonium or potassium persulfate, may be used alone or in conjunction with an accelerator, such as potassium metabisulfite, or sodium thiosulfate. Organic peroxides, such as benzoyl peroxide and t-butyl hydroperoxide are also useful initiators. The initiator and accelerator, commonly referred to as catalyst, may be used in proportions of 0.1 percent to 10 percent each based on the weight of monomers to be copolymerized. The amount, as indicated above, may be adjusted to control the intrinsic viscosity of the polymer. The temperature may be from room temperature to 60° C. or more as is conventional.

Suitable dispersing agents useful in emulsion polymerization include anionic types such as the sodium salts of the higher fatty acid sulfates, such as that of lauryl alcohol, the higher fatty acid salts, such as the oleates or stearates or morpholine, 2-pyrrolidone, triethanolamine or mixed ethanolamines, or any of the nonionic types, such as ethylene oxidemodified alkyl phenols, of which tert-octyl phenol modified by 20 to 40 ethylene oxide units is representative, ethylene oxide-modified higher fatty alcohols such as lauryl alcohol, containing 20 to 50 ethylene oxide units, similarly modified long-chain mercaptans, fatty acids, amines, or the like. Mixtures of nonionic and anionic dispersing agents are also useful.

The elements of the pad, in addition to the crushed foam, are the liquid-impermeable film and the absorbent material.

Suitable flexible liquid-impermeable films include polyolefins such as polyethylene and polypropylene, saran, and the like.

Among useful absorbent materials, preferably nontextile materials, held between the impermeable film and the crushed foam; are cellulosic waddings made from wood pulp, cotton or rayon; carded, garnetted or other open wood, cotton or rayon fibers, crepe paper or tissue paper layers and even hydrophobic fibers which give a capillary effect, such as polyolefins, polyesters, acrylics, polyvinyls and the like, spongy materials, etc.

EXAMPLE 1

An emulsion copolymer dispersion prepared from 2574 parts deionized water, 87 parts sodium lauryl sulfate, 90 parts acrylic acid, 315 parts acrylamide, 900 parts acrylonitrile, and 7695 parts n-butyl acrylate is compounded in the following formulation:

|  | Product | Solids |
|---|---|---|
| Dispersion | 200 | 100 |
| Titanium Dioxide (Titanox RA-45) | 25 | 25 |
| Clay (Acme WW) | 30 | 30 |
| Melamine-Formaldehyde (Resin Aerotex MW) | 4.6 | 3.7 |
| Ammonium Stearate | 14 | 4.6 |
| Water | 70 | — |
| Ammonia (28%) | 4 | — |
|  | 347.6 | 163.3 |
| Solids - 47.0% | | |

All parts and percentages are by weight unless otherwise stated.

Foam is made by whipping air into the formulation using a Kitchen-Aid Mixer (Model C) to a wet density of about 0.16 g./cc. The foam is then cast at 40 mils onto release paper and dried for 1.75 minutes at 280° F. This is then placed with the foam side adjacent an opened (fluffed) absorbent wood pulp laying loosely on a polyethylene film of about the same width as the foam. The laminate is then passed between rollers heated to 250°–300° F. This crushes the dry foam to about 8 mils thick, and firmly bonds the foam to the wadding. The release paper is then peeled off. To achieve more complete crosslinking of the foam, the composite is heated in an oven for 2 minutes at 300° F. The crushed foam has a cold-flex temperature of −15° F.

By following substantially the same procedure as above but by placing the foam on a non-woven layer and then placing on the absorbent layer with the non-woven side adjacent the absorbent layer, there is produced a surface with extremely soft hand which when bonded to a liquid impermeable layer or a woven or non-woven gauze affords a comfortable absorbent pad.

EXAMPLE 2

Example 1 is repeated except that 135 parts of itaconic acid, 315 parts of acrylamide, 5850 parts of ethyl acrylate, 405 parts of acrylonitrile and 2305 parts of n-butyl acrylate are used as the monomers for the foam.

The wet foam is placed directly on the non-woven. The coated material is dried at 280° F. for 1.5 minutes and then passed through nip rollers to crush the foam. The crushed foam coated non-woven is then cured by heating at 300° F. for two minutes.

EXAMPLE 3

Example 1 is repeated except that for the foam 90 parts acrylic acid, 315 parts acrylamide, 675 parts of acrylonitrile and 8920 parts of n-butyl acrylate are used. The resultant crushed foam has a cold flex temperature of 15° F.

EXAMPLE 4

Example 1 is repeated except that 180 parts of acrylic acid, 315 parts of acrylamide, 900 parts of acrylonitrile and 7605 parts of n-butyl acrylate are used as the monomers, for the foam.

EXAMPLE 5

Example 1 is repeated except that 45 parts of acrylic acid, 315 parts of acrylamide, 1800 parts of acrylonitrile and 6840 parts of n-butyl acrylate are used as the monomers, for the foam.

EXAMPLE 6

Example 1 is repeated but the monomers for the foam consist of 270 parts methacrylic acid, 180 parts acrylamide, 375 parts acrylonitrile, 2250 parts butyl acrylate, and 5925 parts ethyl acrylate.

EXAMPLE 7

The procedure described in Example 6 is repeated except the methacrylic acid is replaced with 45 parts of itaconic acid and the amount of butyl acrylate is changed to 2475 parts.

EXAMPLE 8

The procedure described in Example 1 is followed with an emulsion polymer of 170 parts itaconic acid, 200 parts methacrylic acid, 135 parts acrylamide, 450 parts acrylonitrile, 2700 parts butyl acrylate, and 3485 parts ethyl acrylate, to prepare the foam.

EXAMPLE 9

The procedure described in Example 1 is carried out with an emulsion polymer of 135 parts methacrylic acid, 180 parts acrylamide, 630 parts acrylonitrile, 5400 parts butyl acrylate, and 3655 parts isopropyl acrylate.

EXAMPLE 10

Example 1 is repeated with an emulsion polymer of 135 parts itaconic acid, 270 parts acrylamide, 630 parts acrylonitrile, 5400 parts butyl acrylate, 1285 parts ethyl acrylate, and 1285 parts methyl acrylate, as the foam. Similar results are obtained when isobutyl acrylate or 2-ethylhexyl acrylate are used in place of butyl acrylate or ethyl acrylate.

EXAMPLE 11

Example 1 is repeated with latices of polymers having the composition:
a. 86EA/10AN/2MIAM/2AM
b. 65EA/25.5BA/4.5AN/3.5AM/1.5IA
c. 96EA/2MIAM/2AM
d. 48EA/48BA/3MIAM/1IA with the wet density of between about 0.1 to 0.5 g./cc. at wet thicknesses between about 4 mils and 45 mils. Polymer (a) is relatively hydrophilic, (b) and (c) moderately so, and (d) relatively hydrophobic. All quickly absorbed pipetted water. The lower thicknesses tend to provide a textile-like feel whereas the higher thicknesses give a plastic-like feel.

At a wet density of about 0.18 g./cc. (about 11 lb./ft.$^3$) the crushed density is about 20–40 lbs./ft.$^3$ (but variable because of intertwining with the cellulosic fiber of the wadding used). Pore sizes of the dried cured crushed foams, on the exposed horizontal face of this wet density (about 0.18 g./cc.) are about 1–5 mils with about $10^2$ to $3 \times 10^2$ pores per linear inch and $10^4$ to $10^5$/in.$^2$.

EXAMPLE 12

An emulsion copolymer dispersion is prepared by the procedure described in Example I employing 912 parts deionized water, 47 parts of an alkylaryl polyether alcohol (Triton ®-X-405), 19 parts sodium lauryl sulfate, 91 parts N-methylolacrylamide, 500 parts ethylene and 914 parts vinyl acetate.

EXAMPLE 13

An emulsion copolymer dispersion is prepared by the procedure described in Example I from 950 parts deionized water, 62 parts of an alkylaryl polyether alochol (Triton-X-405), 74 parts N-methyiolacrylamide, 635 parts ethylene and 810 parts vinyl chloride.

EXAMPLE 14

Example I is repeated except that 180 parts of acrylic acid, 4000 parts of butadiene, and 4820 parts of styrene are used as the monomers for the foam.

EXAMPLE 15

The following crushed foam formulation was prepared:

|  | Product | Solids |  |
|---|---|---|---|
| Latex (Ex. 11b) | 100 | 50 | (65EA/25.5BA/4.5AN/3.5AM/1.5IA) |
| TiO$_2$ (50% dispersion) | 25 | 12.5 |  |
| Acme WW Clay | 15 | 15 |  |
| H$_2$O | 18.7 | — |  |
| Aerotex MW | 2.3 | 1.8 | Melamine-formaldehyde resin |
| Ammonium Stearate | 7.0 | 2.3 |  |
| NH$_4$OH (28%) | 2.0 | — |  |
|  | 170.0 | 81.6 | Solids - 48.0% |

Foams are made by whipping air into the formulation using a Kitchen-Aid Mixer (Model C) to a density of about 0.18 ± 0.01 g./cc. The foam is then cast at either 45 mils or 7 mils wet on release paper and then dried for 2 minutes or one-half minute, respectively, at 280° F. The foam (still on the release paper) is placed over wadding on polyethylene and the sandwich passed through crush rolls at 60 lb. pressure. The release paper is peeled away and the composite cured at 280° F. for 5 minutes.

The samples are then compared to a commercial product for feel, for rate of absorbence of 5 ml. of water pipeted onto the surface, for surface feel after the water is absorbed (by pressing a palm on the surface) and for wet abrasion resistance by rubbing the wet spot with a forefinger.

The heavy foam add-on (~2.5 oz./yd.$^2$) feels plastic-like but the light add-on (~0.5 oz./yd.$^2$) has a feel more textile-like than the commercial products papery feel. All absorb the water rapidly and feel damp, not wet, after it is absorbed into the nonwoven. All have good wet abrasion resistance; in fact, only after the wadding is moved aside by the rubbing did any of the covers fail. In all respects the low foam add-on appears comparable to the commercial product except it has an improved textile feel.

The following explains the abbreviations used in the foregoing examples:

| EA | ethyl acrylate |
|---|---|
| BA | butyl acrylate |
| AN | acrylonitrile |
| MIAM | methylolacrylamide |
| AM | acrylamide |
| IA | itaconic acid |

I claim:
1. A flexible, absorbent pad comprising a top layer of polymeric foam material permeable to liquids, an underlying layer of liquid-absorbent material and a bottom film of flexible moisture-impervious material, the improvement in which said polymeric foam material is crushed foam of an addition polymer derived from an aqueous polymer latex, said addition polymer having a soft monomer component and a hard monomer component, said soft monomer component containing butadiene, ethylene/vinyl acetate, ethylene/vinyl chloride, propylene/vinyl acetate or propylene/vinyl chloride, the thickness of the crushed layer being from about 1 mil to about 10 mils, and the pore size being less than about 10 mils with approximately 100,000 to 1,000,000 pores per square inch.

2. A flexible, absorbent pad comprising a top layer of polymeric foam material permeable to liquids, an underlying layer of liquid-absorbent material, and a bottom layer of a woven or non-woven gauze, wherein said polymeric foam material is crushed foam of an addition polymer comprising an acrylic monomer, the thickness of the crushed layer being from about 1 mil to about 10 mils and the pore size being less than about 10 mils with approximately 100,000 to 1,000,000 pores per square inch.

3. The article of claim 2 in which the addition polymer is a crosslinked thermoset foam, and in which the absorbent material is fibrous, with intimate intertwining of the fiber and the foam at their juncture but with a substantial thickness of the absorbent material free of foam and with a substantial thickness of the foam free of fiber.

4. The article of claim 2 in which reaction products of one or more of a crosslinking group of the structure —OH, —SH, >NH,

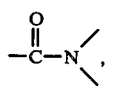

—N=C=O, 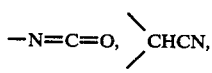

—CHC=O, and 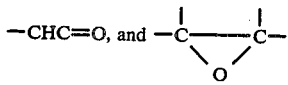

provides the crosslinking.

5. The article of claim 4 in which the foam contains a polymerized unsaturated acid and the crosslinking is provided by a water soluble condensate of formaldehyde with urea, N,N'-ethyleneurea, a dihydroxyethyl urea, or a triazine, the thickness of the crushed foam being less than about 5 mils.

6. The article of claim 2 wherein the copolymer is composed of itaconic acid, acrylamide, ethyl acrylate, acrylonitrile, and n-butyl acrylate.

7. The article of claim 2 wherein said addition polymer has a soft monomer component and a hard monomer component, said soft monomer component containing butadiene, ethylene/vinyl acetate, ethylene/vinyl chloride, propylene/vinyl acetate or propylene/vinyl chloride.

* * * * *